United States Patent
Hecker et al.

(10) Patent No.: US 8,783,470 B2
(45) Date of Patent: Jul. 22, 2014

(54) METHOD AND APPARATUS FOR PRODUCING AUTOLOGOUS THROMBIN

(75) Inventors: Barry F. Hecker, Pierceton, IN (US); Michael D. Leach, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 13/480,852

(22) Filed: May 25, 2012

(65) Prior Publication Data

US 2012/0228203 A1 Sep. 13, 2012

Related U.S. Application Data

(62) Division of application No. 12/399,048, filed on Mar. 6, 2009, now Pat. No. 8,187,475.

(51) Int. Cl.
*C02F 1/38* (2006.01)
*B01D 24/00* (2006.01)
*B01D 35/18* (2006.01)
*B01D 29/07* (2006.01)

(52) U.S. Cl.
USPC ............ 210/360.1; 210/380.1; 210/499; 210/175; 210/660

(58) Field of Classification Search
CPC .................................................. C12N 9/6429
USPC .......... 119/14.03, 14.08, 14.11, 14.18, 14.01, 119/712, 720, 721; 210/380.1, 360.1, 499, 210/405, 175, 660, 319, 358, 173, 512.2, 210/782; 424/529–532; 422/101, 44
See application file for complete search history.

(56) References Cited

U.S. PATENT DOCUMENTS

| | | | |
|---|---|---|---|
| 280,820 A | 7/1883 | Hickson et al. | |
| 593,333 A | 11/1897 | Park | |
| 1,468,313 A | 9/1923 | Lux | |
| 1,593,814 A | 7/1926 | Vogel | |
| 2,722,257 A | 11/1955 | Lockhart | |

(Continued)

FOREIGN PATENT DOCUMENTS

| | | |
|---|---|---|
| AU | 696278 | 1/1999 |
| BR | 9103724 | 3/1993 |

(Continued)

OTHER PUBLICATIONS

"Cell Isolation Techniques, Methods and Materials, Working with Enzymes," (2004) (9 pages) Worthington Biochemical Corp.

(Continued)

Primary Examiner — Ana Fortuna
(74) Attorney, Agent, or Firm — Harness, Dickey

(57) ABSTRACT

A device for isolating a component of a multi-component composition. The device includes a housing, a chamber, and a withdrawal port. The chamber is rotatably mounted within the housing. The chamber includes a chamber base and a sidewall. The side wall extends from the chamber base. At least a portion of the sidewall is defined by a filter that permits passage of a first component of the multi-component composition out of the chamber through the filter and to the housing base. The filter restricts passage of a second component of the multi-component composition through the filter. The withdrawal port extends from a position proximate to the housing base to an exterior of the device. The withdrawal port permits the withdrawal of the first component from the housing base to an exterior of the device.

19 Claims, 7 Drawing Sheets

(56) References Cited

U.S. PATENT DOCUMENTS

| | | | |
|---|---|---|---|
| 3,013,557 A | 12/1961 | Pallotta |
| 3,141,846 A | 7/1964 | Laven, Jr. |
| 3,159,159 A | 12/1964 | Cohen |
| 3,300,051 A | 1/1967 | Mitchell |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,583,627 A | 6/1971 | Wilson |
| 3,593,915 A | 7/1971 | Steinacker |
| 3,596,652 A | 8/1971 | Winkelman |
| 3,647,070 A | 3/1972 | Adler |
| 3,654,925 A | 4/1972 | Holderith |
| 3,661,265 A | 5/1972 | Greenspan |
| 3,706,305 A | 12/1972 | Berger et al. |
| 3,706,306 A | 12/1972 | Berger et al. |
| 3,723,244 A | 3/1973 | Breillatt, Jr. |
| 3,741,400 A | 6/1973 | Dick |
| 3,779,383 A | 12/1973 | Ayres |
| 3,785,549 A | 1/1974 | Latham, Jr. |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,066,549 A | 1/1978 | Oeser et al. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies et al. |
| 4,159,896 A | 7/1979 | Levine et al. |
| 4,187,979 A | 2/1980 | Cullis et al. |
| 4,189,385 A | 2/1980 | Greenspan |
| 4,203,840 A | 5/1980 | Stoeppler et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies et al. |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,443,345 A | 4/1984 | Wells |
| 4,445,550 A | 5/1984 | Davis et al. |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,790,942 A * | 12/1988 | Shmidt et al. ............ 210/650 |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,835 A | 7/1989 | Grande |
| 4,846,974 A | 7/1989 | Kelley et al. |
| 4,850,952 A | 7/1989 | Figdor et al. |
| 4,853,137 A | 8/1989 | Ersson et al. |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,909,251 A | 3/1990 | Seelich |
| 4,911,847 A * | 3/1990 | Shmidt et al. ............ 210/650 |
| 4,915,847 A | 4/1990 | Dillon et al. |
| 4,917,801 A | 4/1990 | Luderer et al. |
| 4,928,603 A | 5/1990 | Rose et al. |
| 4,929,242 A | 5/1990 | Desecki et al. |
| 4,933,291 A | 6/1990 | Daiss et al. |
| 4,939,081 A | 7/1990 | Figdor et al. |
| 4,943,273 A | 7/1990 | Pages et al. |
| 4,946,601 A | 8/1990 | Fiehler |
| 4,950,220 A | 8/1990 | Wells et al. |
| 4,957,637 A | 9/1990 | Cornell |
| 4,957,638 A | 9/1990 | Smith |
| 4,973,168 A | 11/1990 | Chan |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |

(56) References Cited

U.S. PATENT DOCUMENTS

| | | |
|---|---|---|
| 5,024,613 A | 6/1991 | Vasconcellos et al. |
| 5,030,215 A | 7/1991 | Morse et al. |
| 5,030,341 A | 7/1991 | McEwen et al. |
| 5,039,401 A | 8/1991 | Columbus et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker et al. |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,370,221 A | 12/1994 | Magnusson et al. |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,480,378 A | 1/1996 | Weis-Fogh et al. |
| 5,484,383 A | 1/1996 | Fitch, Jr. et al. |
| 5,486,359 A | 1/1996 | Caplan et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,601,711 A | 2/1997 | Sklar et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas et al. |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh et al. |
| 5,643,193 A | 7/1997 | Papillon et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Ievine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,795,489 A | 8/1998 | Holm et al. |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,853,600 A | 12/1998 | McNeal et al. |
| 5,860,937 A | 1/1999 | Cohen |
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,899,874 A | 5/1999 | Jonsson et al. |
| 5,900,245 A | 5/1999 | Sawhney et al. |
| 5,906,934 A | 5/1999 | Grande et al. |

(56) References Cited

U.S. PATENT DOCUMENTS

| | | |
|---|---|---|
| 5,916,557 A | 6/1999 | Berlowitz-Tarrant et al. |
| 5,916,743 A | 6/1999 | Lake et al. |
| 5,918,622 A | 7/1999 | Perez et al. |
| 5,924,972 A | 7/1999 | Turvaville et al. |
| 5,934,803 A | 8/1999 | Hutter |
| 5,938,621 A | 8/1999 | Kelly et al. |
| 5,951,160 A | 9/1999 | Ronk |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,961,210 A | 10/1999 | McCardel et al. |
| 5,980,734 A | 11/1999 | Itoh et al. |
| 5,980,757 A | 11/1999 | Brown et al. |
| 5,985,315 A | 11/1999 | Patat et al. |
| 5,997,544 A | 12/1999 | Nies et al. |
| 6,007,811 A | 12/1999 | Sawyer et al. |
| 6,010,627 A | 1/2000 | Hood, III |
| 6,011,490 A | 1/2000 | Tonnesen et al. |
| 6,020,196 A | 2/2000 | Hu et al. |
| 6,022,306 A | 2/2000 | Dumont et al. |
| 6,025,201 A | 2/2000 | Zelmanovic et al. |
| 6,027,655 A | 2/2000 | Holm |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,123,655 A | 9/2000 | Fell et al. |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,286,670 B1 | 9/2001 | Smith |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,334,842 B1 | 1/2002 | Hlavinka et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | DiCesare et al. |
| 6,409,528 B1 | 6/2002 | Bodnar |
| 6,410,344 B1 | 6/2002 | Chung et al. |
| 6,417,004 B1 | 7/2002 | Brady et al. |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B1 | 10/2002 | Coelho et al. |
| 6,487,992 B1 * | 12/2002 | Hollis ............................ 119/712 |
| 6,508,778 B1 | 1/2003 | Verkaart et al. |
| 6,516,953 B1 | 2/2003 | DiCesare et al. |
| 6,523,698 B1 | 2/2003 | Dennehey et al. |
| 6,544,162 B1 | 4/2003 | Van Wie et al. |
| 6,544,727 B1 | 4/2003 | Hei |
| 6,558,341 B1 | 5/2003 | Swisher |
| 6,563,953 B2 | 5/2003 | Lin et al. |
| 6,596,180 B2 | 7/2003 | Baugh et al. |
| 6,623,959 B2 | 9/2003 | Harris |
| 6,629,919 B2 | 10/2003 | Egozy et al. |
| 6,638,503 B2 | 10/2003 | Chitte et al. |
| 6,676,629 B2 | 1/2004 | Andrew et al. |
| 6,716,187 B1 | 4/2004 | Jorgensen et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,764,531 B2 | 7/2004 | Hogan |
| 6,777,231 B1 | 8/2004 | Katz et al. |
| 6,803,022 B2 | 10/2004 | DiCesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Wells et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,077,827 B2 | 7/2006 | Greenfield |
| 7,155,288 B2 | 12/2006 | Soykan et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero et al. |
| 7,354,515 B2 | 4/2008 | Coull et al. |
| 7,374,678 B2 | 5/2008 | Leach et al. |
| 7,411,006 B2 | 8/2008 | Shanbrom |
| 7,470,371 B2 | 12/2008 | Dorian et al. |
| 7,531,355 B2 | 5/2009 | Rodriguez et al. |
| 7,553,413 B2 | 6/2009 | Dorian et al. |
| 7,694,828 B2 | 4/2010 | Swift et al. |
| 7,708,152 B2 | 5/2010 | Dorian et al. |
| 7,806,276 B2 | 10/2010 | Leach et al. |
| 7,824,559 B2 | 11/2010 | Dorian et al. |
| 7,845,499 B2 | 12/2010 | Higgins et al. |
| 7,866,485 B2 | 1/2011 | Dorian et al. |
| 7,901,584 B2 | 3/2011 | Dorian et al. |
| 7,914,689 B2 | 3/2011 | Higgins et al. |
| 7,987,995 B2 | 8/2011 | Dorian et al. |
| 8,012,077 B2 | 9/2011 | Hoeppner |
| 8,048,321 B2 | 11/2011 | Leach et al. |
| 8,062,534 B2 | 11/2011 | Higgins et al. |
| 8,096,422 B2 | 1/2012 | Dorian et al. |
| 8,105,495 B2 | 1/2012 | Dorian et al. |
| 8,133,389 B2 | 3/2012 | Dorian et al. |
| 8,142,342 B2 | 3/2012 | Hoeppner |
| 8,187,475 B2 | 5/2012 | Hecker et al. |
| 8,337,711 B2 | 12/2012 | Dorian et al. |
| 8,567,609 B2 | 10/2013 | Landrigan et al. |
| 2001/0009757 A1 | 7/2001 | Bischof et al. |
| 2002/0032112 A1 | 3/2002 | Pages |
| 2002/0035820 A1 | 3/2002 | Farris |
| 2002/0076400 A1 | 6/2002 | Katz et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2002/0192632 A1 | 12/2002 | Hei et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |

(56) References Cited

U.S. PATENT DOCUMENTS

| | | |
|---|---|---|
| 2003/0082152 A1 | 5/2003 | Hedrick et al. |
| 2003/0185803 A1 | 10/2003 | Kadiyala et al. |
| 2003/0191429 A1 | 10/2003 | Andrew et al. |
| 2003/0205538 A1 | 11/2003 | Dorian et al. |
| 2004/0005246 A1 | 1/2004 | Efthimiadis et al. |
| 2004/0013575 A1 | 1/2004 | Stevens et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2004/0238445 A1* | 12/2004 | McLaughlin et al. ........ 210/645 |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0109716 A1 | 5/2005 | Leach et al. |
| 2005/0130301 A1 | 6/2005 | McKay et al. |
| 2005/0145187 A1* | 7/2005 | Gray ............................ 119/174 |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0196393 A1 | 9/2005 | Shanbrom |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0051865 A1 | 3/2006 | Higgins et al. |
| 2006/0057693 A1 | 3/2006 | Simon |
| 2006/0083720 A1 | 4/2006 | Fraser et al. |
| 2006/0140923 A1 | 6/2006 | Evangelista et al. |
| 2006/0151384 A1 | 7/2006 | Ellsworth et al. |
| 2006/0175242 A1 | 8/2006 | Dorian et al. |
| 2006/0175244 A1 | 8/2006 | Dorian et al. |
| 2006/0178610 A1 | 8/2006 | Nowakowski |
| 2006/0196885 A1 | 9/2006 | Leach et al. |
| 2006/0243676 A1 | 11/2006 | Swift et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0208321 A1 | 9/2007 | Leach et al. |
| 2008/0011684 A1 | 1/2008 | Dorian et al. |
| 2008/0164204 A1 | 7/2008 | Hatamian et al. |
| 2008/0173593 A1 | 7/2008 | Coull et al. |
| 2008/0193424 A1 | 8/2008 | McKale et al. |
| 2008/0210645 A1 | 9/2008 | Coull et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2008/0318317 A1 | 12/2008 | Roche et al. |
| 2009/0014391 A1 | 1/2009 | Leach et al. |
| 2009/0018313 A1 | 1/2009 | Shanbrom |
| 2009/0101599 A1 | 4/2009 | Dorian et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0289014 A1 | 11/2009 | Hoeppner |
| 2010/0055087 A1 | 3/2010 | Higgins et al. |
| 2010/0140182 A1 | 6/2010 | Chapman et al. |
| 2010/0186676 A1* | 7/2010 | Van Der Berg ............ 119/14.08 |
| 2010/0206798 A1 | 8/2010 | Dorian et al. |
| 2010/0226909 A1 | 9/2010 | Hecker et al. |
| 2010/0256595 A1 | 10/2010 | Leach et al. |
| 2010/0323870 A1 | 12/2010 | Leach et al. |
| 2010/0324450 A1 | 12/2010 | Leach et al. |
| 2011/0014705 A1 | 1/2011 | Leach et al. |
| 2011/0020196 A1 | 1/2011 | Grippi et al. |
| 2011/0021334 A1 | 1/2011 | Leach et al. |
| 2011/0036786 A1 | 2/2011 | Ellsworth |
| 2011/0056893 A1 | 3/2011 | Leach et al. |
| 2011/0065183 A1 | 3/2011 | Dorian et al. |
| 2011/0077596 A1 | 3/2011 | Higgins et al. |
| 2011/0168193 A1 | 7/2011 | Leach et al. |
| 2011/0192804 A1 | 8/2011 | Landrigan et al. |
| 2011/0251041 A1 | 10/2011 | Chavarria et al. |
| 2012/0015796 A1 | 1/2012 | Leach et al. |
| 2012/0228203 A1 | 9/2012 | Hecker et al. |
| 2014/0051061 A1* | 2/2014 | Landrigan et al. ................ 435/2 |
| 2014/0091048 A1* | 4/2014 | Leach et al. .................. 210/789 |

FOREIGN PATENT DOCUMENTS

| | | |
|---|---|---|
| CA | 1321138 | 8/1993 |
| CA | 2182862 | 6/1996 |
| CA | 2448415 A1 | 12/2002 |
| CN | 1074709 | 7/1993 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0244834 A2 | 11/1987 |
| EP | 0253198 | 1/1988 |
| EP | 0272915 A2 | 6/1988 |
| EP | 285891 | 10/1988 |
| EP | 0295771 | 12/1988 |
| EP | 0417818 | 3/1991 |
| EP | 534178 | 3/1993 |
| EP | 0534178 | 3/1993 |
| EP | 0592242 | 4/1994 |
| EP | 1005910 | 6/2000 |
| EP | 1006360 A2 | 6/2000 |
| EP | 1289618 | 3/2003 |
| EP | 1406492 B1 | 4/2004 |
| EP | 1427279 A1 | 6/2004 |
| EP | 1467746 A2 | 10/2004 |
| EP | 1509326 | 3/2005 |
| EP | 1670315 A2 | 6/2006 |
| EP | 1716901 | 11/2006 |
| GB | 854715 | 11/1960 |
| JP | 60-053845 | 3/1985 |
| JP | 60250014 A | 12/1985 |
| JP | 63182055 A | 7/1988 |
| JP | 6454256 | 4/1989 |
| JP | 2036872 | 2/1990 |
| JP | 02071747 | 3/1990 |
| JP | 04500170 T | 1/1992 |
| JP | 6250014 A | 9/1994 |
| JP | 09187504 A | 7/1997 |
| JP | 9509432 T | 9/1997 |
| JP | 11502502 T | 3/1999 |
| JP | 2000117150 A | 4/2000 |
| JP | 02129224 | 10/2000 |
| JP | 2001017540 A | 1/2001 |
| JP | 2004-305439 A | 11/2004 |
| JP | 200598704 | 4/2005 |
| JP | 2005523128 T | 8/2005 |
| JP | 2005524451 | 8/2005 |
| JP | 2006-305365 A | 11/2006 |
| MX | 246078 | 5/2007 |
| WO | WO-8400905 | 3/1984 |
| WO | WO-8802259 | 4/1988 |
| WO | WO-8901827 A1 | 3/1989 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9616714 A1 | 6/1996 |
| WO | WO-9617871 | 6/1996 |
| WO | WO-9617871 A1 | 6/1996 |

(56) References Cited

FOREIGN PATENT DOCUMENTS

| WO | WO-9848938 A1 | 11/1998 |
|---|---|---|
| WO | WO-0061256 | 10/2000 |
| WO | WO-0074713 A1 | 12/2000 |
| WO | WO-0103756 | 1/2001 |
| WO | WO-0183068 | 11/2001 |
| WO | WO-0224107 | 3/2002 |
| WO | WO-0238610 A1 | 5/2002 |
| WO | WO-02060925 A1 | 8/2002 |
| WO | WO-02098566 A2 | 12/2002 |
| WO | WO-03015800 | 2/2003 |
| WO | WO-03024215 A1 | 3/2003 |
| WO | WO-03053362 A2 | 7/2003 |
| WO | WO-03088905 | 10/2003 |
| WO | WO-03090839 A1 | 11/2003 |
| WO | WO-03092894 | 11/2003 |
| WO | WO-03099412 A1 | 12/2003 |
| WO | WO-2004009207 | 1/2004 |
| WO | WO-2004037427 A1 | 5/2004 |
| WO | WO-2004104553 | 12/2004 |
| WO | WO-2005034843 A2 | 4/2005 |
| WO | WO-2006081699 A1 | 8/2006 |
| WO | WO-2007127834 A2 | 11/2007 |
| WO | WO-2007142908 A1 | 12/2007 |
| WO | WO-2009021257 A1 | 2/2009 |
| WO | WO-2009111338 A1 | 9/2009 |
| WO | WO-2011008836 A1 | 1/2011 |

OTHER PUBLICATIONS

"Cell Isolation Theory, Tissue Types," (2004) (5 pages) Worthington Biochemical Corp.

"Cytori Celution Cell Concentrate Device," Exhibit 14, 510(k) Summary, FDA approval K060482 (Sep. 28, 2006).

"Frequently Asked Questions, 1. Kits, 2. Enzymes," (2003) 3 pages Worthington Biochemical Corp.

"Sefar Solutions for the Healthcare Industry," brochure (2003) 9 pages Sefar Medifab®.

"Trypsinizing cells." Bart's Cookbook, Web. Apr. 14, 2010. http://pingu.salk.edu/~sefton/Hyper_protocols/trypsin.html.

Anesthesiology, vol. 81, No. 4, pp. 1074-1077, Oct. 1994, Hiromasa Mitsuhata, M.D., et al., "An Anaphylactic Reaction to Topical Fibrin Glue".

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31:3 (1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105: 5 (1993): 892-7.

Clotalyst™ Autologous Thrombin Heater Operators Manual, Biomet Biolgics, Inc., 23 pages.

Biopolymers, vol. 27, pp. 763-774, 1988, Gerald Marx, "Mechanism of Fibrin Coagulation Based on Selective, Cation-Driven, Protofibral Association".

Boomgaard, et al., "Pooled Platelet Concentrates Prepared by the Platelet-Rich-Plasma Method and Filtered with Three Different Filters and Stored for 8 Days." Vox Sanq, vol. 68: 82-89, Feb. 1995.

Casali, B., F. Rodeghiero, A. Tosetto, B. Palmieri, R. Immovilli, C. Ghedini, and P. Rivasi. "Fibrin glue from single-donation autologous plasmapheresis." Transfusion 32:7 (1992): 641-3.

Clotalyst™ Autologous Clotting Factor by Biomet Biologics, Inc. brochure 12 pages (2006).

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May 1976).

DelRossi, A. J., A. C. Cernaianu, R. A. Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100:2 (Aug. 1990): 281-6.

DePalma, L., et al., "The preparation of fibrinogen concentrate for use as fibrin glue by four different methods." Transfusion (1993) vol. 33, No. 9; pp. 717-720.

DeUgarte, M.D., Daniel A., et al., "Future of Fat as Raw Material for Tissue Regeneration," (Feb. 2003) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., vol. Philadelphia: W.B. Saunders Company, 1992.

Epstein, G. H., R. A. Weisman, S. Zwillenberg, and A. D. Schreiber. "A new autologous fibrinogen-based adhesive for otologic surgery." *Ann Otol Rhinol Laryngol* 95 (May 25-26, 1985) 40-5.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (Aug. 15, 1975): 495-501.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Friesen, M.D., Robert, et al. "Blood Conservation During Pediatric Cardiac Surgery: Ultrafiltration of the Extracorporeal Circuit Volume After Cardiopulmonary Bypass." Anesth. Analg 1993: 77-702-7.

Gibble, J. W. and P. M. Ness. "Fibrin glue: the perfect operative sealant?" *Transfusion* 30 (1990): 741-7.

Gimble, Jeffrey M., "Adipose-Derived Stem Cells for Regenerative Medicine," Circulation Research (May 11, 2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (Feb. 29, 2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Guilak, Frank, et al., "Adipose-derived adult stem cells for cartilage tissue engineering," Biorheology 41 (2004) pp. 389-399, IOS Press.

(56) References Cited

OTHER PUBLICATIONS

Harris, E.L.V. Concentration of the Extract. In. Protein Purification Methods: A Practical Approach Harris, E.L.V.; Angel, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.

Hattori, et al., "Osteogenic Potential of Human Adipose Tissue-Derived Stromal Cells as an Alternative Stem Cell Source," Cells Tissues Organs (2004) 178:2-12 Karger.

Hennis, H. L., W. C. Stewart, and E. K. Jeter. "Infectious disease risks of fibrin glue [letter]." *Ophthalmic Surg* 23 (Sep. 1992): 640.

Hood, Andrew G., et al., "Perioperative Autologous Sequestration III: A New Physiologic Glue with Wound Healing Properties," (Jan. 1993) vol. 14 pp. 126-129.

International Preliminary Examination Report and Written Opinion issued Aug. 31, 2010 for PCT/US2009/035564 claiming benefit of U.S. Appl. No. 61/078,178, filed Jul. 3, 2008 of which U.S. Appl. No. 12/395,085, filed Feb. 27, 2009 claims benefit.

International Preliminary Report on Patentability mailed Feb. 12, 2009, for PCT/US2007/017055 filed Jul. 31, 2007, which claims benefit of U.S. Appl. No. 60/834,550, filed Jul. 31, 2006, based on U.S. Appl. No. 60/723,312, filed Oct. 4, 2005; U.S. Appl. No. 60/654,718, filed Feb. 17, 2005; and U.S. Appl. No. 60/651,050, filed Feb. 7, 2005.

International Search Report and Written Opinion for PCT/US2006/003597 mailed Feb. 6, 2006.

International Search Report and Written Opinion for PCT/US2006/003599 mailed Aug. 21, 2006.

International Search Report and Written Opinion mailed Aug. 12, 2008 for PCT/US07/17055.

International Search Report and Written Opinion mailed Jul. 3, 2009 for PCT/US2009/035564 claiming benefit of U.S. Appl. No. 61/078,178, filed Jul. 3, 2008.

Jackson, C. M. and Y. Nemerson. "Blood coagulation." *Annu Rev Biochem* 49 (1980): 765-811).

Journal of Biomaterials Applications, vol. 7, pp. 309-353, Apr. 1993, David H. Sierra, "Fibrin Sealant Adhesive Systems: A review of their Chemistry, Material Properties and Clinical Applications".

Journal of Oral Maxillofacial Surgery, vol. 43, pp. 605-611, Helene Matras, M.D., "Fibrin Seal: The State of the Art" (1985).

Kjaergard, H. K., U. S. Weis-Fogh, H. Sorensen, J. Thiis, and I. Rygg. "A simple method of preparation of autologous fibrin glue by means of ethanol." *Surg Gynecol Obstet* 175 (1992): 72-3.

Kjaergard, H. K., Fogh Us Weis, and J. J. Thiis. "Preparation of autologous fibrin glue from pericardial blood." *Ann Thorac Sur* 55 (1993): 543-4.

Laryngoscope vol. 99, pp. 974-976, Sep. 1989, Kyosti Laitakari, M.D., et al., "Autologous and Homologous Fibrinogen Sealants: Adhesive Strength".

Laryngoscope, vol. 95, pp. 1074-1076, Sep. 1985, Karl H. Siedentop, M.D., et al., "Autologous Fibrin Tissue Adhesive".

Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".

Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.

Lerner, R. and N. S. Binur. "Current status of surgical adhesives." *J Surg Res* 48 (Feb. 1990): 165-81.

Longas, Maria O., "An Improved Method for the Purification of Human Fibrinogen." J. Biochem (1980) vol. 11, pp. 559-564.

Marrowstim™ Concentration System, (2008) 20 pages Biomet Biologics, Inc.

Marx, Gerard, et al., "Heat Denaturation of Fibrinogen to Develop a Biomedical Matrix." Journal of Biomedical Materials Research Part B: Applied Biomaterials (Apr. 2007) pp. 49-57.

Masri, Marwan A., et al. "Isolation of Human Fibrinogen of High Purity and in High Yield Using Polyethylene Glycol 1000." Thromb Haemostas (Struttgart) (1983) vol. 49 (2); pp. 116-119.

Matras, Helene, H. P. Dinges, H. Lassmann, and B. Mamoli. "Zur nahtlosen interfaszikularen Nerventransplantation im Tierexperiment." Wein Med Woschtr 122:37 (1972): 517-523.

Moretz, W., Jr., J Shea Jr., J. R. Emmett, and J Shea. "A simple autologous fibrinogen glue for otologic surgery." *Otolaryngol Head Neck Surg* 95 (Jul. 1986): 122-4.

Nakagami, Hironori, et al., "Novel Autologous Cell Therapy in Ischemic Limb Disease Through Growth Factor Secretion by Cultured Adipose Tissue-Derived Stromal Cells," Angiogenesis by Adipose Tissue-Derived Cells, (Dec. 2005) pp. 2542-2547, American Heart Association, Inc.

Nathan, Suresh,, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.

Office Action mailed Apr. 6, 2010 for Japanese Application No. 2007-554193 filed Aug. 23, 2007 has been provided including a partial translation thereof, which cites JP11-502502 and JP2001017540. Japanese Application No. 2007-554193 claims benefit of PCT/US2006/003599, filed Jan. 30, 2006; claiming priority from U.S. Appl. Nos. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Office Action mailed Apr. 6, 2010 for Japanese Application No. 2007554191 filed Aug. 7, 2007 has been provided including a partial translation thereof, which also cites JP2001017540. Japanese Application No. 2007554191 claims benefit of PCT/US2006/003597, filed Jan. 30, 2006; claiming priority from U.S. Appl. Nos. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Office Action mailed Sep. 14, 2010 for Japanese Application No. 2007-554193 filed Aug. 23, 2007 has been provided including a partial translation thereof. Japanese Application No. 2007-554193 claims benefit of PCT/US2006/003599, filed Jan. 30, 2006; claiming priority from U.S. Appl. Nos. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Office Action mailed Sep. 14, 2010 for Japanese Application No. 2007554191 filed Aug. 7, 2007 has been provided including a partial translation thereof. Japanese Application No. 2007554191 claims benefit of PCT/US2006/003597, filed Jan. 30, 2006; claiming priority from U.S. Appl. Nos. 60/651,050, filed Feb. 7, 2005; U.S. Appl. No. 60/654,718, filed Feb. 17, 2005; and U.S. Appl. No. 60/723,312, filed Oct. 4, 2005 of which U.S. Appl. No. 11/831,605, filed Jul. 31, 2007 and U.S. Appl. No. 12/772,497, filed May 3, 2010 claim benefit.

Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).

Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".

Parker, Anna M., et al., "Adipose-derived stem cells for the regeneration of damaged tissues," Expert Opinion, Cell- & Tissue-based Therapy, Expert Opin. Biol. Ther. (2006) pp. 567-578 Informa UK Ltd.

Planat-Bénard, V., et al., "Spontaneous Cardiomyocyte Differentiation From Adipose Tissue Stroma Cells," Adipose-Derived Cell Cardiomyocyte (Feb. 6, 2004) pp. 223-229 American Heart Association, Inc.

Plasmax™ Plasma Concentrate, brochure (2006) 5 pages Biomet Biologics, Inc.

Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.

(56) References Cited

OTHER PUBLICATIONS

Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Apr. 15, 2007) pp. 1409-1422.
Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (Apr. 15, 2007) pp. 1423-1424.
Sanal, M. "Does fibrin glue cause foreign body reactions? [letter]." *Eur J Pediatr Surg* 3 (1992): 190 (1 page).
Sanal, M., H. Dogruyol, A. Gurpinar, and O. Yerci. "Does fibrin glue cause foreign body reactions?" *Eu r J Pediatr Surg* 2 (1992): 285-6.
Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (Apr. 10, 2007) pp. 818-827 AlphaMed Press.
Sigma-Aldrich® Alkaline Phosphatase (Procedure No. 85), drug fact sheet, (2003) pp. 1-2, Sigma-Aldrich, Inc.
Silver, Frederick H., et al., "Review Preparation and use of fibrin glue in surgery." Biomaterials 16 (1995) pp. 891-903.
Solem, Jan Otto, et al., "Hemoconcentration by Ultrafiltration During Open-Heart Surgery," Scand J Thor Cardiovasc Surg 22:271-274, 1988.
Sutton, Robin G., et al. "Comparison of Three Blood-Processing Techniques During and After Cardiopulmonary Bypass." Ann Thorac Surg (1993) vol. 56; pp. 941-943.
Takahashi, Kazutoshi et al., "Induction of Pluripotent Stem Cells from Adult Human Fibroblasts by Defined Factors," Cell, (Nov. 30, 2007) pp. 1-12, Elsevier Inc.
The American Journal of Surgery, vol. 168, pp. 120-122, Aug. 1994, Roy L. Tawes, Jr., M.D., et al., "Autologous Fibrin Glue: The Last Step in Operative Hemostatis".
The American Surgeon, vol. 55, pp. 166-168, Mar. 1989, William D. Spotnitz, M.D., et al., "Successful Use of Fibrin Glue During 2 Years of Surgery at a University Medical Center".
Vortech™ Concentration System, "Do you want a sticky gel to improve the handling of your bone graft?, Platelet Rich Plasma Concentrate, High Volume in 5 Minutes," Biomet Biologics, Inc., Aug. 2005.
Weis-Fogh, U. S. "Fibrinogen prepared from small blood samples for autologous use in a tissue adhesive system." *Eur Surg* Res 20 (1988): 381-9.
Weisman, MD., Robert A., "Biochemical Characterization of Autologous Fibrinogen Adhesive," Laryngoscope 97: Oct. 1987; pp. 1186-1190.
Wiseman, David M., David T. Rovee, and Oscar M. Alverez. "Wound Dressings: Design and Use." In *Wound Healing: Biochemical & Clinical Aspects*, ed. I. Kelman Cohen, Robert F. Diegelmann, and William J. Lindblad. 562-580. 1st ed., vol. Philadelphia: W. B. Saunders Company, 1992.
Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.
Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.
Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.
"Caps for Corning® and Costar® Plastic Labware," Technical Bulletin. (Dec. 2008) Corning, Incorporated.
"Centrifuge Tubes" Corning Costar brochure. 1996/1997 Catalog pp. 76-77.
"Clotalyst® Autologous Clotting Factor" brochure. (Aug. 15, 2008) Biomet Biologics.
"Clotalyst® Autologous Clotting Factor. Would you like to have an autologous thrombin for rapid clotting and haemostasis?" Brochure. Biomet Biologics (Aug. 15, 2008).
"Corning® 15 and 50 mL Centrifuge Tubes," Life Sciences. (Jun. 2005) Corning Incorporated.
"Isolation and characterization of cells from rat adipose tissue developing into adipocytes," (1978) vol. 19, Journal of Lipid Research, pp. 316-324.
"Letter CryoSeal FS System. Vaccines, Blood & Biologics," letter. (Jul. 26, 2007) FDA U.S. Food and Drug Administation. http://www.fda.gov/BiologicsBloodVaccines/BloodBloodProducts/ApprovedProducts/PremarketApprovalsPMAs/ucm091631.htm (Web accessed Aug. 12, 2011).
"MarrowStim™ Concentration Kit Peripheral Arterial Disease (PAD) Study" brochure. Web. Jul. 2, 2009 http://www.biomet.com/patients/clinical_recruitment_padstudy.cfm.
"MarrowStim™ Concentration System," brochure. Biomet Biologics Jun. 15, 2008.
"Plasmax® Plasma Concentration System" brochure. (Jun. 15, 2008) Biomet® Biologics.
"Prosys PRP Kit," brochure Tozai Holdings, Inc. http://tozaiholdings.en.ec21.com/Prosys_PRP_Kit--5467051_5467061.html Printed from Web Aug. 24, 2011.
"Prosys PRP Kit," Tozai Holdings, Inc. EC21 Global B2B Marketplace http://www.ec21.com/product-details/Prosys-PRP-Kit--5467061.html Printed from Web Jul. 18, 2011.
"ThermoGenesis Corp. to Supply Autologous Thrombin Kits to Biomet, Inc.," PR Newslink: http://tinyurl.com/4h3up. (Apr. 5, 2005) http://www.noblood.org/press-releases/2128-thermogenesis-corp-supply-autologous-thrombin-kits-biomet-inc [web accessed Sep. 27, 2011].
"Trypsinization of Adherent Cells," (undated) 2 pages.
Badiavas, et al., "Treatment of Chronic Wounds With Bone Marrow-Derived Cells," (Reprinted) Arch Dermatol. 139:510-516 (Apr. 2003).
Bang, N.U., et al., "Plasma Protein Requirements for Human Platelet Aggregation" Ann. N.Y. Acad Sci, 201:280-299 (1972).
BioCUE™ Platelet Concentration System, Jun. 2010. (2 pages).
Brodke, et al., "Bone Grafts Prepared with Selective Cell Retention Technology Heal Canine Segmental Defects as Effectively as Autograft", SCR-Enriched Bone Grafts Heal Canine Segmental Defects, Journal of Orthopaedic Research (May 2006) pp. 857-866.
Chinese Office Action mailed Nov. 5, 2013 for Chinese Patent Application No. 201080019707.7 filed Apr. 3, 2009.
Clayden J D et al: "Improved segmentation reproducibility in group tractography using a quantitative tract similarity measure" Neuroimage, Academic Press, Orlando, FL, US LNKD-DOI: 10.1016/J.Neuroimage. 2006.07.016, vol. 33, No. 2, Nov. 1, 2006, pp. 482-492.
Clotalyst™ Automatic Clotting Factor, Would you like to have an autologous thrombin for rapid clotting and haemostasis?, brochure, Biomet Biologics, Inc., Feb. 2007 (12 pages).
Connolly, "Injectable Bone Marrow Preparations to Stimulate Osteogenic Repair," Clinical Orthopaedics and Related Research 313:8-18 (Apr. 1995).
Connolly, John, M.D., et al. "Development of an Osteogenic Bone-Marrow Preparation." The Journal of Bone and Joint Surgery, Incorporated. vol. 71-A, No. 5 (Jun. 1989) pp. 684-691.
Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.
De Ugarte, et al., "Comparison of Multi-Lineage Cells from Human Adipose Tissue and Bone Marrow," Cells Tissues Organs 174:101-109 (2003).
De Ugarte, et al., "Differential Expression of Stem Cell Mobilization-Associated Molecules on Multi-Lineage Cells from Adipose Tissue and Bone Marrow," Immunology Letters 89:267-270 (2003).
De Wit, et al. "Experiments on the Preparation of Blood Components with the IBM 2991 Blood Cell Processor" Vox Sang. 29: 352-362 (Feb. 10, 1975).

(56) References Cited

OTHER PUBLICATIONS

Ehricke H H et al: "Visualizing MR diffusion tensor fields by dynamic fiber tracking and uncertainty mapping" Computers and Graphics, Elsevvier, GB LNKD-DOI: 10.1016/J.CAG.2006.01.031, vol. 30, No. 2, Apr. 1, 2006, pp. 255-264.

Eppley, et al., "Platelet Quantification and Growth Factor Analysis from Platelet-Rich Plasma: Implications for Wound Healing," Plastic and Reconstructive Surgery, 114(6):1502-1508 (Nov. 2004).

European Communication Pursuant to Article 94(3) EPC mailed May 6, 2013 for PCT/US2010/029957 which claims benefit of U.S. Appl. No. 12/417,789, filed Apr. 3, 2009.

Fibrostik™ Plasma Concentrator, Attention Operating Surgeon, Cell Factor Technologies, Inc., Jul. 2003.

Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.

Galois, et al., "Cartilage Tissue Engineering: State-of-the-Art and Future Approaches," Pathol Biol (Paris), 53(10), Dec. 2005.

GPS® II System, Gravitational Platelet Separation System, "Accelerating the Body's Natural Healing Process," Biomet Biologics (Jul. 15, 2006) 16 pages.

Grove, et al., "Plasticity of Bone Marrow-Derived Stem Cells," Stem Cells: Concise Review, 22, Jan. 2004.

Harvest SmartPrep PRP-20 Procedure Pack, "Instructions for Use" (date unknown).

Harvest Technologies brochure, SmartPrep2 (2002).

Haynesworth, S.E. et al. "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).

Hemstreet, G., et al., "Tissue Disaggregation of Human Renal Cell Carcinoma with Further Isopyknic and Isokinetic Gradient Purification," Cancer Research, (1980) vol. 40, pp. 1043-1049.

Hernigou, et al., "Percutaneous Autologous Bone-Marrow Grafting for Nonunions. Influence of the Number and Concentration of Progenitor Cells," Journal of Bone & Joint Surgery, 87-A(7):1430-1437 (Jul. 2005).

Hom, D., et al. "Promoting Healing with Recombinant Human Platelet-Derived Growth Factor-BB in a Previously Irradiated Problem Wound." The Laryngoscope, vol. 113 (pp. 1566-1671) Sep. 2003.

International Preliminary Examination Report and Written Opinion issued Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085, filed Feb. 27, 2009.

International Preliminary Report on Patentability and Written Opinion mailed Oct. 13, 2011 for PCT/US2010/029957 which claims benefit of U.S. Appl. No. 12/417,789, filed Apr. 3, 2009.

International Preliminary Report on Patentability and Written Opinion mailed Oct. 31, 2013 for PCT/US2012/034104 claiming benefit of U.S. Appl. No. 13/089,591, filed Apr. 19, 2011.

International Preliminary Report on Patentability completed Aug. 13, 2009 for PCT/US2008/004687 claiming benefit of U.S. Appl. No. 60/911,407, filed Apr. 12, 2007.

International Preliminary Report on Patentability mailed Jan. 26, 2012 for PCT/US2010/041942 claiming benefit of U.S. Appl. No. 12/504,413, filed Jul. 16, 2009.

International Search Report and Written Opinion mailed Aug. 9, 2011 for PCT/US2011/031954 claiming benefit of U.S. Appl. No. 12/758,127, filed Apr. 12, 2010.

International Search Report and Written Opinion mailed Jul. 2, 2008 for International Application No. PCT/US2008/004687 which claims priority to U.S. Appl. No. 60/911,407, filed Apr. 12, 2007.

International Search Report and Written Opinion mailed Jul. 30, 2010 for PCT/US2010/029957 which claims benefit of U.S. Appl. No. 12/417,789, filed Apr. 3, 2009.

International Search Report and Written Opinion mailed Nov. 7, 2011 for PCT/US2011/045290 claiming benefit of U.S. Appl. No. 12/846,944, filed Jul. 30, 2010.

International Search Report and Written Opinion mailed Oct. 8, 2010 for PCT/US2010/041942 claiming benefit of U.S. Appl. No. 12/504,413, filed Jul. 16, 2009.

International Search Report for International Application No. PCT/US/0316506 mailed Oct. 13, 2003 which claims benefit of U.S. Appl. No. 60/383,013, filed May 24, 2002.

International Search Report for International Application No. PCT/US2007/012587 mailed Nov. 6, 2007 which claims benefit of U.S. Appl. No. 11/441,276, filed May 25, 2006.

International Search Report for PCT/US2012/034104 mailed Oct. 29, 2012, claiming benefit of U.S. Appl. No. 13/089,591, filed Apr. 18, 2012.

Invitation to Pay Additional Fees and, Where Applicable, Protest Fee mailed Aug. 6, 2012 for PCT/US2012/034104 claiming benefit of U.S. Appl. No. 13/089,591, filed Apr. 19, 2011.

Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).

Japan Office Action mailed Aug. 23, 2013 for Japan Patent Application No. 2010-503066.

Japan Office Action mailed Jan. 22, 2013 for Japan Application No. 2010-503066.

Jayadev, Suprya. "Trypsinization of Adherent Cells." Aug. 8, 1991. Web. Apr. 14, 2010 http://www.duke.edu/web/ceramide/protocols/0005.html.

Johnstone, et al., "Autologous Mesenchymal Progenitor Cells in Articular Cartilage Repair", Clinical Orthopaedics and Related Research 367S:S156-S162 (Oct. 1999).

Jones D K et al: "Confidence mapping in diffusion ensor magnetic resonance imaging tractography using a bootstrap approach" Magnetic Resonance in Medicine Wiley USA, vol. 53, No. 5, May 2005, pp. 1143-1149.

Jorgensen, et al., "Stem Cells for Repair of Cartilage and Bone: The Next Challenge in Osteoarthritis and Rheumatoid Arthritis," Annals of Rheumatic Diseases, Aug. 2000.

Karpatkin, S., "Heterogeneity of Human Platelets. VI., Correlation of Platelet Function with Platelet Volume", Blood, vol. 51, No. 2 (Feb. 1978).

Kumar, Vijay et al. "Stability of Human Thrombin Produced From 11 ml of Plasma Using the Thrombin Processing Device," Journal of American Society of Extra-Corporeal Technology. JECT: Mar. 2005:37; 390-395.

Kumar, Vijay et al. "Whole Blood Thrombin: Development of a Process for Intra-Operative Production of Human Thrombin." Journal of American Society of Extra-Corporeal Technology. JECT: Apr. 2007; 39:18-23.

Kumar, Vijay et al., "Autologous Thrombin: Intraoperative Production From Whole Blood." Journal of American Society of Extra-Corporeal Technology. JECT: Apr. 2008; 40:94-98.

Lasher, Lisa, M.D., "My Experience with PRP," PowerPoint presentation, http://www.cellfactortech.com/global_products.cfm, printed Sep. 16, 2005.

Lori N F et al: "Diffusion tensor fiber tracking of human brain connectivity: acquisition methods, reliability analysis and biological results" NMR in Biomedicine Wiley UK, vol. 15, No. 7-8, Nov. 2002, pp. 493-515.

Lu, et al., "Bone Marrow Mesenchymal Stem Cells: Progress in Bone/Cartilage Defect Repair," 19(1), Jan. 2002.

Marrowstim Concentration System, Biomet Biologics, Inc., 20 pages (REV Feb. 15, 2008).

Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).

Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).

Minntech® Filtration Technologies Group, "Renaflo® II Hemofilter," Minntech Corporation (2004); http://www.minntech.com/ftg/products/renaflo/index.html, printed Jul. 15, 2004 (2 pages).

(56) References Cited

OTHER PUBLICATIONS

Molnar, Amy, "Stem Cells from Muscles Can Repair Cartilage, Study Finds Genetically Engineered Muscle-Derived Stem Cells Improved Cartilage Repair in Rats", American College of Rheumatology, (2005).

Nilsson, et al., "Bone Repair Induced by Bone Morphogenetic Protein in Ulnar Defects in Dogs," The Journal of Bone and Joint Surgery, vol. 68 B., No. 4, Aug. 1986.

Notice of Allowance mailed Mar. 24, 2011 for U.S. Appl. No. 12/101,586.

Notice of Allowance mailed May 27, 2010 for U.S. Appl. No. 12/101,594, filed Apr. 11, 2008.

Notice of Allowance mailed Oct. 18, 2011 for U.S. Appl. No. 12/897,401.

Office Action (Final) mailed Mar. 18, 2010 for U.S. Appl. No. 12/101,594, filed Apr. 11, 2008.

Office Action mailed Feb. 3, 2011 for U.S. Appl. No. 12/101,586, filed Apr. 14, 2008.

Office Action mailed Nov. 16, 2010 for U.S. Appl. No. 12/897,401 claiming benefit of U.S. Appl. No. 12/101,594, filed Apr. 11, 2008.

Office Action mailed Oct. 16, 2009 for U.S. Appl. No. 12/101,594, filed Apr. 11, 2008.

Office Action mailed Sep. 20, 2010 for U.S. Appl. No. 12/101,586, filed Apr. 14, 2008.

Parchment et al., Roles for in vitro myelotoxicity tests in preclincial drug development and clinical trial planning, Toxicology Pathology, Society of Toxicological Pathologists, vol. 21, No. 2, 1993, pp. 241-250.

Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.

Ponticiello, Michael S., "A Rapid Technique for the Isolation and Concentration of Stem Cells from Human Bone Marrow", Cell Factor Technologies, Inc. (2006) 2 pages.

Rodbell, M., "Metabolism of Isolated Fat Cells: I. Effects of Hormones on Glucose Metabolism and Lipolysis," The Journal of Biological Chemistry, (1964) vol. 239, No. 2, pp. 375-380.

Schmidt, K.G., et al., "Labelling of Human and Rabbit Platelets with Indium-Oxine Complex", 23:97-106 (1979).

Schmidt, K.G., et al., "Preparation of Platelet Suspensions from Whole Blood in Buffer", Scand. J. Hoemato, 23:88-96 (1979).

Semple, Elizabeth, PhD, et al. "Quality of Thrombin Produced From the Patient's Own Plasma Using the TPD™, a New Thrombin-Processing Device." Journal of American Society of Extra-Corporeal Technology. JECT: 2005; 37:196-200.

Sierra, D. H. "Fibrin sealant adhesive systems: a review of their chemistry, material properties and clinical applications." *J Biomater Appl* 7 (Apr. 1993): 309-52.

Swift, Mathew J., et al., "Characterization of Growth Factors in Platelet Rich Plasma," 1-Cell Factor Technologies, http://www.cellfactortech.com/global_products.cfm, printed Sep. 16, 2005.

Symphony II Platelet Concentrate System/PCS brochure; "Increasing bone graft bioactivity through reproducible concentrations of natural growth factors," DePuy (Jan. 2003).

The Sports Medicine Center, "Knee Cartilage Implantation", Carticel™, "Autologous Cultured Chondrocyte Implantation", http://www.orthoassociates.com/carticel.htm (printed Apr. 6, 2006).

The Stone Clinic, "Platelet Rich Plasma (PRP)", web site printed May 2006.

Woodell-May, et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).

Written Opinion of the International Preliminary Examining Authority mailed Mar. 17, 2009 for International Application No. PCT/US2008/004687 which claims priority to U.S. Appl. No. 60/911,407, filed Apr. 12, 2007.

English translation dated Jan. 13, 2014 for Japanese patent application No. JP2005-98704.

\* cited by examiner

METHOD AND APPARATUS FOR PRODUCING AUTOLOGOUS THROMBIN

CROSS-REFERENCE TO RELATED APPLICATIONS

This application is a divisional of U.S. patent application Ser. No. 12/399,048 filed on Mar. 6, 2009, now U.S. Pat. No. 8,178,475. The entire disclosure of the above application is incorporated herein by reference.

FIELD

The present disclosure relates to methods and devices for isolating components of a multi-component composition, such as isolating thrombin from whole blood or plasma.

BACKGROUND

The statements in this section merely provide background information related to the present disclosure and may not constitute prior art.

Thrombin, which is found naturally in whole blood, plays an important role in the blood clotting process. Specifically, thrombin is an enzyme of blood plasma that catalyzes the conversion of fibrinogen to fibrin, the last block of the blood clotting process. Thus, the clotting process can be enhanced by isolating fibrinogen and thrombin from whole blood or plasma and introducing increased amounts of these blood components to a wound site. While current methods and devices for isolating thrombin are suitable for their intended use, they are subject to improvement.

SUMMARY

The present teachings provide for a device for isolating a component of a multi-component composition. The device includes a housing, a chamber, and a withdrawal port. The chamber is rotatably mounted within the housing. The chamber includes a chamber base and a sidewall. The side wall extends from the chamber base. At least a portion of the sidewall is defined by a filter that permits passage of a first component of the multi-component composition out of the chamber through the filter and to the housing base. The filter restricts passage of a second component of the multi-component composition through the filter. The withdrawal port extends from a position proximate to the housing base to an exterior of the device. The withdrawal port permits the withdrawal of the first component from the housing base to an exterior of the device.

The present teachings further provide for a method for isolating thrombin from a multi-component composition. The method includes the following: loading the composition into a chamber rotatably mounted in a housing, the chamber including glass beads and polyacrylimide beads; loading reagent into the chamber; rotating the chamber at a first speed for a first time period to mix the contents of the chamber and form a mixture; rotating the chamber at a second speed for a second time period to cause thrombin to separate from the mixture and pass through a filter of the chamber and collect outside of the chamber; and extracting the thrombin from within the housing.

The present teachings further provide for a method for isolating thrombin from a multi-component composition. The method includes the following: forming a solution including about 24 cc of the composition, about 8 grams of glass beads, about 4.5 grams of polyacrylimide beads, and about 8 cc of reagent; mixing the solution for about one minute at about 50 rpm; and rotating the solution at a speed of from about 1,500 rpm to about 3,500 rpm for about two minutes to separate thrombin from the solution.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
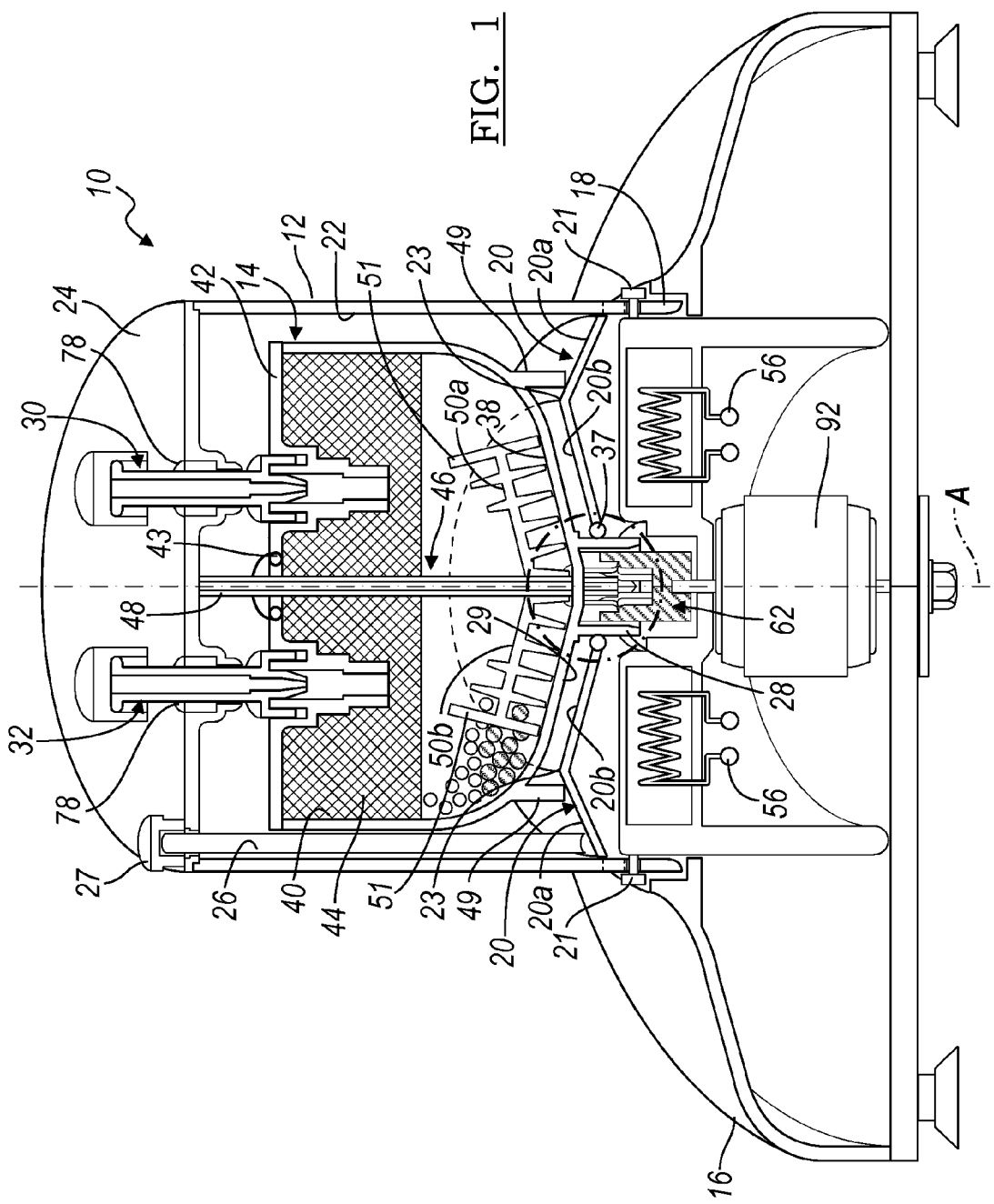
FIG. 1 is a cross-sectional view of a component isolation device according to the present teachings seated on a torque generating device.
Figure 2:
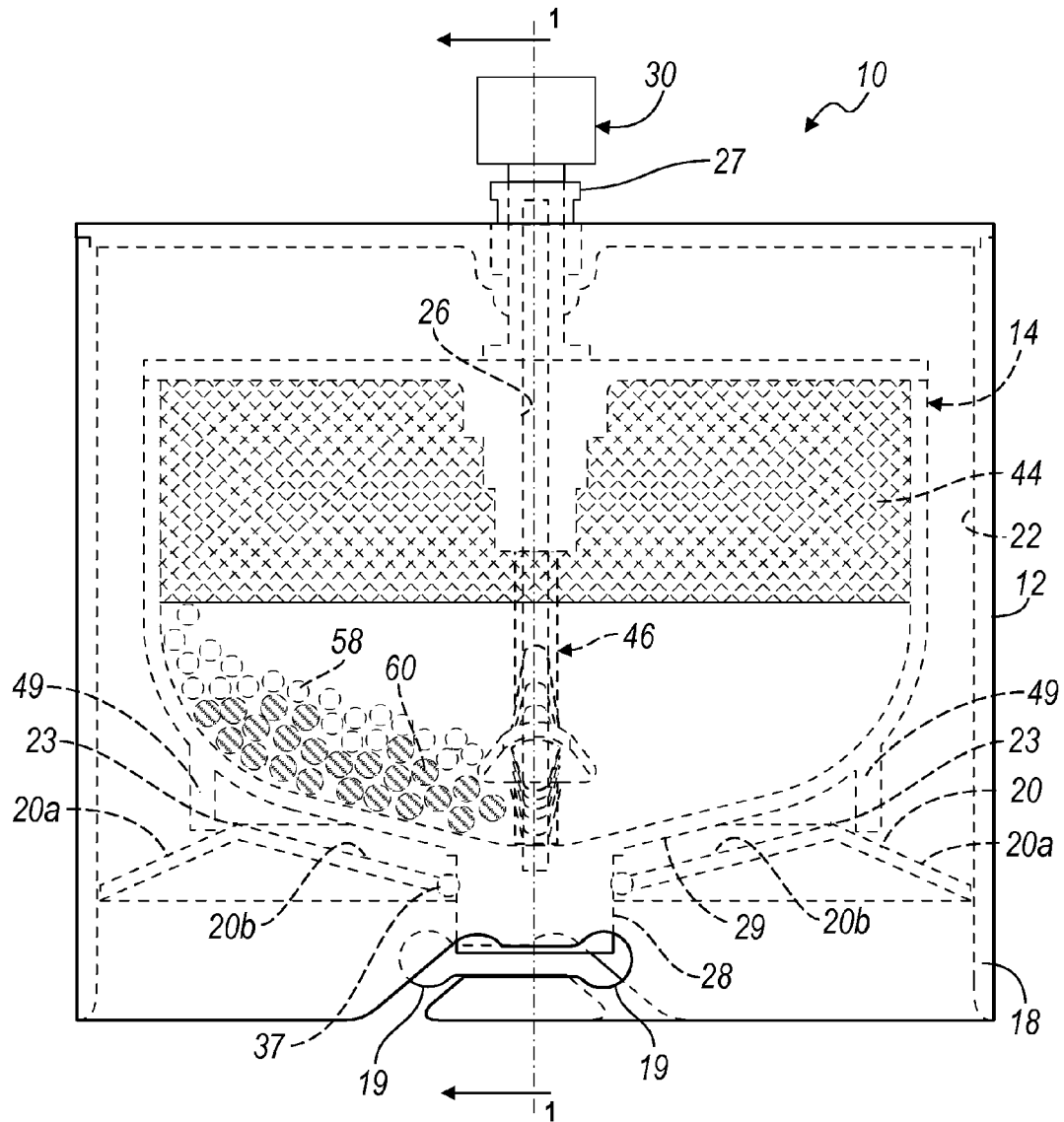
FIG. 2 is a side view of the component isolation device of FIG. 1.
Figure 3:
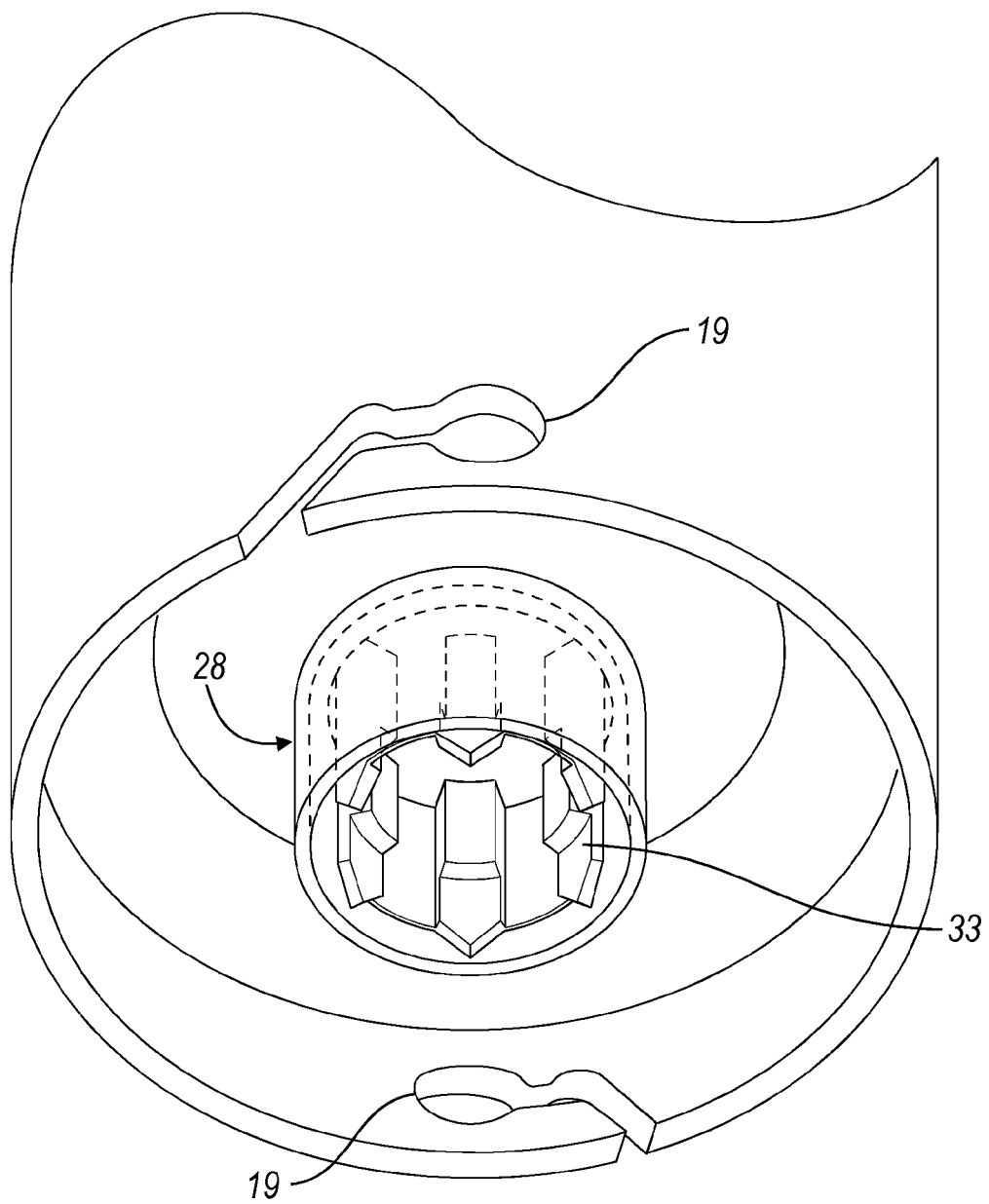
FIG. 3 is a bottom perspective view of the component isolation device of FIG. 1.

With initial reference to FIGS. 1-3, a device for isolating one or more components of a multi-component composition is illustrated at reference numeral 10. The device 10 generally includes a housing 12 and a chamber 14 rotatably mounted within the housing 12. The chamber 14 is generally cylindrical and is rotated by a torque generating device 16.

The housing 12 generally includes a substantially cylindrical support portion 18, a base portion 20, a sidewall 22, a cover 24, an aspiration port 26, and an axially concentric drive receptor 28.

The cylindrical support portion 18 extends from the base portion 20. The cylindrical support portion 18 includes a pair of locking slots 19. The locking slots 19 (see FIG. 2) cooperate with tabs 21 of the torque generating device 16 to secure the housing 12 to the torque generating device 16.

The base portion 20 is between the sidewall 22 and the support portion 18. The base portion 20 includes a first sloped portion 20a and a second sloped portion 20b. The first sloped portion 20a is proximate to the sidewall 22 and slopes toward the sidewall 22. The second sloped portion 20b is distal to the sidewall 22 and extends to an axis of rotation A of the chamber 14. The second sloped portion 20b slopes away from the sidewall 22. The first sloped portion 20a meets the second sloped portion 20b at an apex portion 23. The first sloped portion 20a directs materials deposited on the first sloped portion 20a toward the sidewall 22 where the materials can be removed from the device 10 through the aspiration port 26.

The drive receptor 28 extends from an under surface 29 of the chamber 14 along the axis of rotation A of the chamber 14. The drive receptor is mounted to the base portion 20 with one or more bearings 37 to permit the chamber 14 to rotate within the housing 12. The drive receptor 28 can be any suitable device for cooperating with the torque generating device 16 to transfer torque from the device 16 to the chamber 14. For example and with reference to FIG. 3, the drive receptor 28 includes an outer cylinder 31 and a series of pointed prongs 33 within the outer cylinder 31. The prongs 33 are sized and shaped to cooperate with a motor connector 62 of the torque generating device 16.

The cover 24 is mounted to an end of the sidewall 22 opposite to the base portion 20. In some applications, the cover 24 is removable. A first inlet subassembly 30 and a second inlet subassembly 32 extend through openings in the cover 24 to provide fluid communication through the cover 24 into the chamber 14. The inlet subassemblies 30 and 32 can be any suitable type of inlet or port and are further described herein.

The aspiration port 26 extends through the cover 24 to a point proximate to the base portion 20. The aspiration port 26 is proximate to the sidewall 22 and extends parallel to the sidewall 22. The aspiration port 26 includes a removable aspiration cap 27.

The chamber 14 includes a chamber base 38, a generally cylindrical chamber sidewall 40 extending from the chamber base 38, and a chamber cover 42. A portion of the chamber sidewall 40 proximate to the chamber cover 42 includes a filter 44 having numerous openings. The filter 44 extends around the cylindrical chamber sidewall 40. The filter 44 can be mounted to the sidewall 40 in any suitable manner, such as with ultrasonic welding.

The filter 44 can be any suitable filter capable of permitting the passage of the components of the multi-composition that are desired for collection through the aspiration port 26 and restricting passage of other materials. For example, the filter 44 can be made of a fabric that is cross woven to form openings in the fabric.

Suitable fabrics can include polyester, such as polyethylene terephthalate (PET). An exemplary filtration fabric for use in filter 44 includes Sefar Medifab® product number 07-15/9 by Sefar, Inc. of Ruschlikon, Switzerland. This product is made of PET monofilament and includes the following properties: a weave pattern of about 2:2 twill weave; a mesh opening having a width of about of 15 µm, +/−2.0 µm; a mesh count of about 194.0 n/cm (n/cm=10'000/(mesh opening+ wire diameter)); a wire diameter of about 37 µm; an open area of about 8.5% (($a_o$) [%]=$(w)^2 \times 100/(w+d)^2$); a thickness of about 55 µm; a weight of about 45 g/m²; and a medical washed finish.

A mixing paddle 46 is mounted within the chamber 14. The mixing paddle 46 includes a main portion 48 and a branched portion 50. The main portion 48 is mounted to the cover 24. The main portion 48 extends through an opening in the chamber cover 42 to within the chamber 14 to a point proximate to the chamber base 38. The branched portion 50 includes two extending portions 50a and 50b that extend from the main portion 48 and are positioned at 180° to each other. The extending portions 50a and 50b extend at an angle so that they are always proximate to the chamber base 38, which slopes upward from the axis of rotation A. The extending portions 50a and 50b each include fins 51 that protrude from the extending portions 50a and 50b at right angles.

The mixing paddle 46 is fixedly mounted to the cover 24 such that it remains stationary to mix the contents of the chamber 14 when the chamber 14 is rotating. A bearing 43 is between the chamber cover 42 and the main portion 48 to permit the chamber cover 42 to rotate about the main portion 48.

An annular rim 49 extends from the undersurface 29 of the chamber base 38. The annular rim 49 is positioned proximate to the apex portion 23 between the apex portion 23 and the sidewall 22. The annular rim 49 prevents material exiting the chamber 14 through the filter 44 from passing over the apex portion 23 to the second sloped portion 20b. The annular rim 49 keeps material exiting the chamber 14 on the first sloped portion 20a, whereby the material can be withdrawn through the aspiration port 26.

Figure 4:
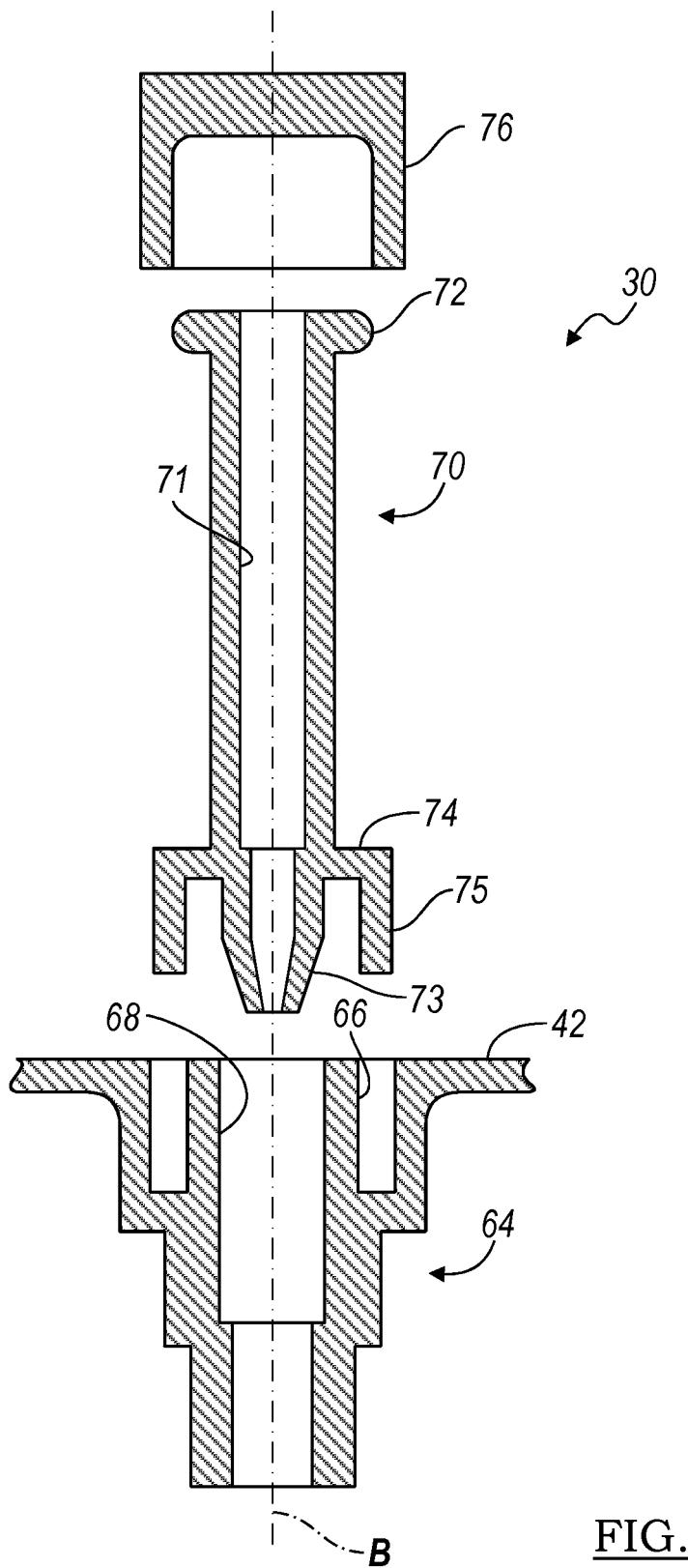
FIG. 4 is a cross-sectional view of an inlet subassembly of the component isolation device of FIG. 1.

With additional reference to FIG. 4, the first inlet assembly 30 includes an inlet tube 64 provided in the chamber cover 42. The inlet tube 64 includes an annular receptor 66. The inlet tube 64 defines a passageway 68 through the chamber cover 42. A sterile filter (not shown) can be positioned in the passageway 68 of the inlet tube 64. The sterile filter can be any suitable filter for preventing the passage of undesirable materials, such as contaminants, beads, clotted portions of blood, etc. For example, the filter can be a syringe filter having openings sized between about 40 and about 100 microns. The passageway 68 can further include a seal (not shown) to prevent contaminants from passing into the chamber 14. The seal can be penetrable to permit introduction of materials into the chamber 14, such as by a syringe used to load the reagent or blood into the chamber 14.

The inlet assembly 30 further includes a removable inlet tube 70 that defines a through bore 71. The removable tube 70 includes an integral Luer fitting 72 at a first end and a tapered portion 73 at a second end opposite to the first end. Proximate to the second end is a plate 74 extending outward from the removable inlet tube 70. The plate 74 extends approximately perpendicular to a longitudinal axis B of the through bore 71. An integral cylindrical flange 75 extends perpendicular to the plate 74. The cylindrical flange 75 is sized to engage the annular receptor 66. The inlet assembly 30 further includes a cap 76 that cooperates with the Luer fitting 72 to provide a sterile closure of the removable tube 70 prior to use, such as during shipment and handling.

As illustrated in FIGS. 1 and 2, prior to use, the removable tube 70 is positioned such that it extends through an opening 78 in the cover 24 of the housing 12 and through the inlet tube 64 of the chamber cover 42 so that the through bore 71 provides a passageway from the exterior of the device 10 to within the chamber 14. In particular, the removable tube 70 is positioned such that the flange 75 is seated within the annular receptor 66 of the chamber cover 42. The removable tube 70, in passing through both the cover 24 and the chamber cover 42, locks the chamber 14 in position and prevents the chamber 14 from rotating during shipment and storage. After a multi-component composition is introduced into the chamber 14 through the first inlet assembly 30, the removable tube 70 is removed, thereby unlocking the chamber 14 to permit the chamber 14 to rotate about the axis of rotation A. The second inlet assembly 32 is substantially similar to the first inlet assembly 30. Therefore, the above description of the first inlet assembly 30 also applies to the second inlet assembly 32.

Figure 5:
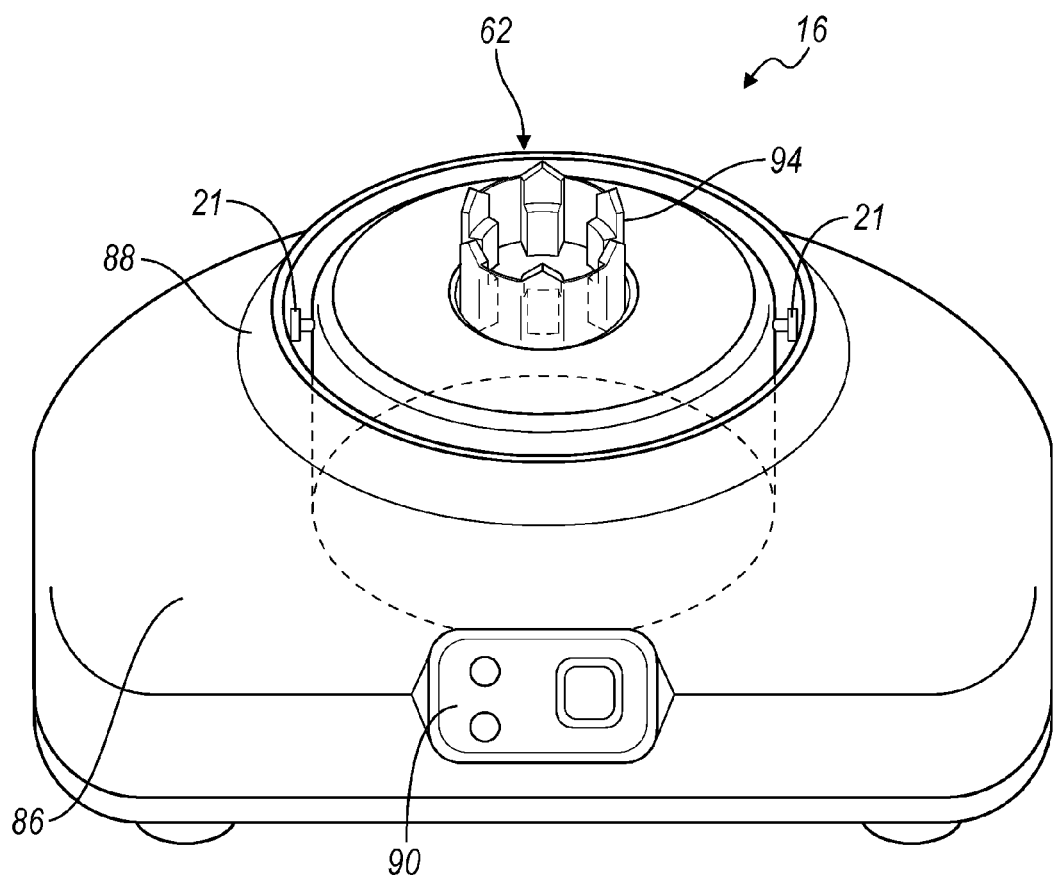
FIG. 5 is a top perspective view of the torque generating device.

With additional reference to FIG. 5, the torque generating device 16 can be any suitable torque generating device. For example, the torque generating device 16 can be a Vortech® base by Biomet Biologics, LLC of Warsaw, Ind., such as disclosed in United States Patent Publication No. 2006/0175244 (application Ser. No. 11/342,749) filed on Jan. 30, 2006, which is hereby incorporated by reference. As illustrated, the torque generating device 16 includes a base 86 having a raised annular support surface 88 and a control panel 90. At a center of the raised annular support surface 88 is the motor connector 62 that is connected to a motor 92 (FIG. 1) of the torque generating device 16. The motor connector 62 is rotated by the motor 92. The motor 92 is controlled using the control panel 90. The motor connector 62 includes a plurality of receptors 94 that cooperate with the prongs 33 of the drive receptor 28 to transfer torque generated by the motor to the drive receptor 28 to rotate the chamber 14.

The torque generating device 16 further includes a heater 56 (FIG. 1). The heater 56 is used to heat the contents of the chamber 14. The heater 56 can be any suitable heater, such as an induction heater, a conduction heater, or an infra-red heater. When the heater 56 is an induction heater, a metal insert can be positioned at the bottom of the chamber 14 and the torque generating device 16 can include a heating coil to conduct current between the device 16 and the chamber 14 to heat the metal insert and ultimately the chamber 14 and its contents.

The device 10 can be used to isolate components of a variety of multi-component compositions. For example, the device 10 can be used to isolate thrombin from whole blood and thrombin from plasma, including platelet rich plasma and platelet rich plasma concentrate.

Figure 6:
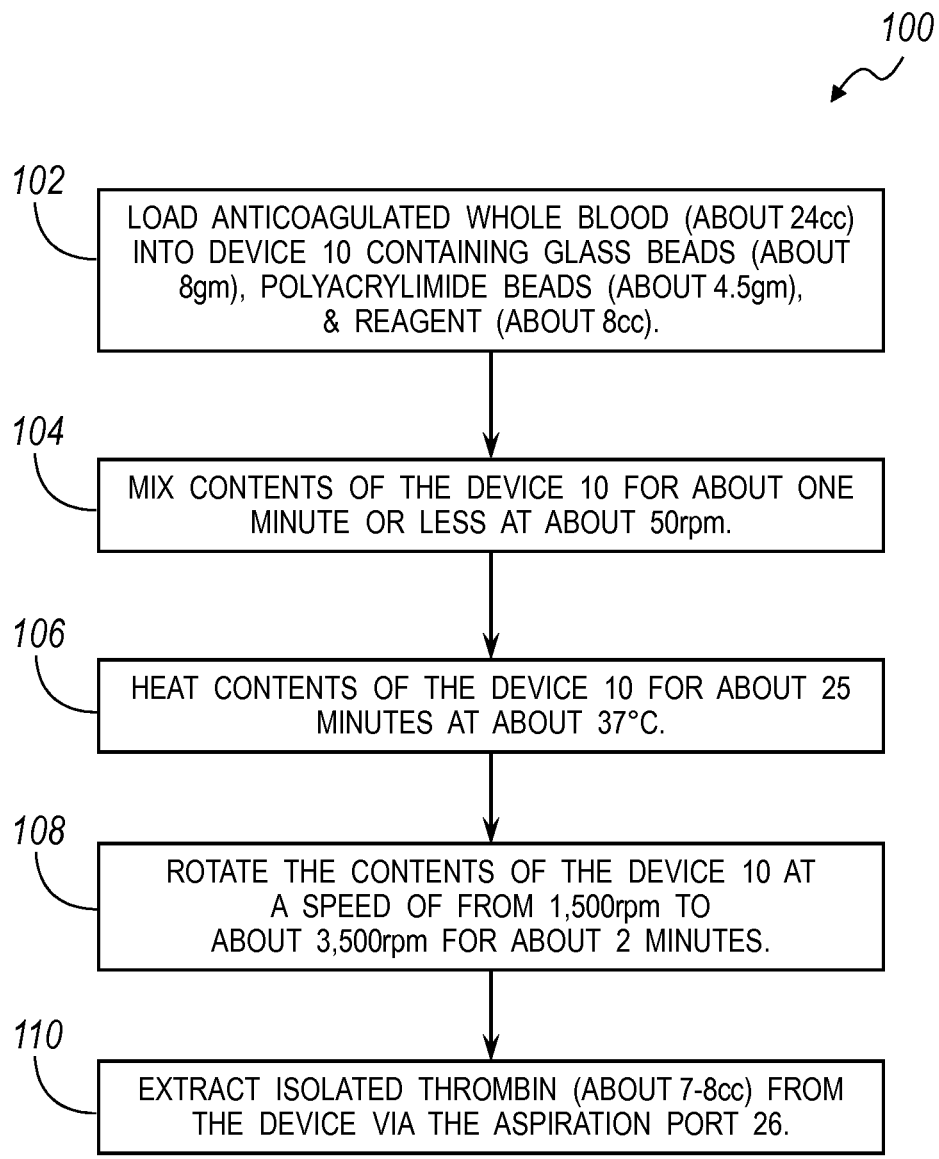
FIG. 6 illustrates a method according to the present teachings for isolating thrombin from whole blood.

With additional reference to FIG. 6, a method for isolating thrombin from whole blood according to the present teachings is at reference number 100. With initial reference to block 102, a suitable amount of anticoagulated whole blood, either autologous or nonautologous, is loaded into the chamber 14 of the device 10. Any suitable amount of whole blood can be used, such as about 24 cc. The blood is loaded through the first inlet assembly 30. A suitable reagent, such as a calcium based compound, is also loaded into the chamber 14. The reagent can include any suitable calcium based compound with or without a suitable alcohol. An exemplary suitable reagent includes calcium chloride and ethanol.

The reagent is loaded through the second inlet assembly 32. Any suitable amount of reagent can be used, such as about 8 cc. The presence of the first and the second inlet assemblies 30 and 32 is advantageous because it provides for a more aseptic process whereby the seal of each of the inlet assemblies is only penetrated once.

To facilitate activation of blood platelets, glass beads 58 are included in the chamber 14. Polyacrylimide beads 60 are also included in the chamber 14. The beads 58 and 60 are typically loaded into the chamber 14 by the manufacturer. Any suitable amount of glass beads 58 and polyacrylimide beads 60 can be used, such as about 8 grams of glass beads and about 4.5 grams of polyacrylimide beads. After the whole blood and reagent are loaded into the chamber 14, the removable tubes 70 are removed from the first and the second inlet assemblies 30 and 32 to permit the chamber 14 to rotate freely within the housing 12.

At block 104, the whole blood, the glass beads 58, the polyacrylimide beads 60, and the reagent, which are all present in the chamber 14, are mixed. The contents of the chamber 14 are mixed by placing the device 10 on the annular support surface 88 of the torque generating device 16. Torque generated by the torque generating device 16 is transferred to the chamber 14 through the interaction between the motor connector 62 and the drive receptor 28 to rotate the chamber 14. The chamber 14 is rotated for about one minute or less at about 50 rpm. The fixed mixing paddle 46 present in the chamber 14 facilitates mixing of the contents of the chamber 14.

At block 106, the contents of the chamber 14 are optionally heated or incubated by the heater 56 for about 25 minutes at about 37° C. The incubation process causes the red blood cells of the whole blood to activate and form a clot, thereby releasing thrombin. After the incubation process, the chamber 14 is rotated at a speed of from about 1,500 rpm to about 3,500 rpm for about 2 minutes at block 108 to separate the contents. The polyacrylimide beads 60 remove excess water from the mixture to increase the concentration of thrombin. For example, use of 4.5 grams of polyacrylimide beads 60, which is more than is typically used, can result in isolation of thrombin that is concentrated at six to seven times.

The rotation at an increased speed (block 108) causes thrombin to separate from the mixture and rise to the area of the filter 44. The openings of the filter 44 are sized to permit the passage of thrombin through the filter 44. The openings of the filter 44 are not large enough to permit the glass beads 58 and polyacrylimide beads 60 to pass through the filter 44. Therefore, the glass beads 58 and the polyacrylimide beads 60 remain within the chamber 14.

Thrombin passes through the filter 44 and settles outside of the chamber 14 on the first sloped portion 20a of the base portion 20. The thrombin can slide down the sidewall 22 to reach the first sloped portion 20a. Due to the presence of the annular rim 49 and because the first sloped portion 20a is sloped toward the sidewall 22, the thrombin is directed toward the sidewall 22 where it can be extracted from the device 10 through the aspiration port 26. At block 110, thrombin can then be extracted through the aspiration port 26 using any suitable device, such as a syringe. Typically, about 7-8 cc of thrombin can be extracted. Thus, the method 100 isolates thrombin of increased concentration from autologous or nonautologous whole blood. As set forth below, the isolated thrombin can be used in a variety of ways to enhance the blood clotting and healing process.

Figure 7:
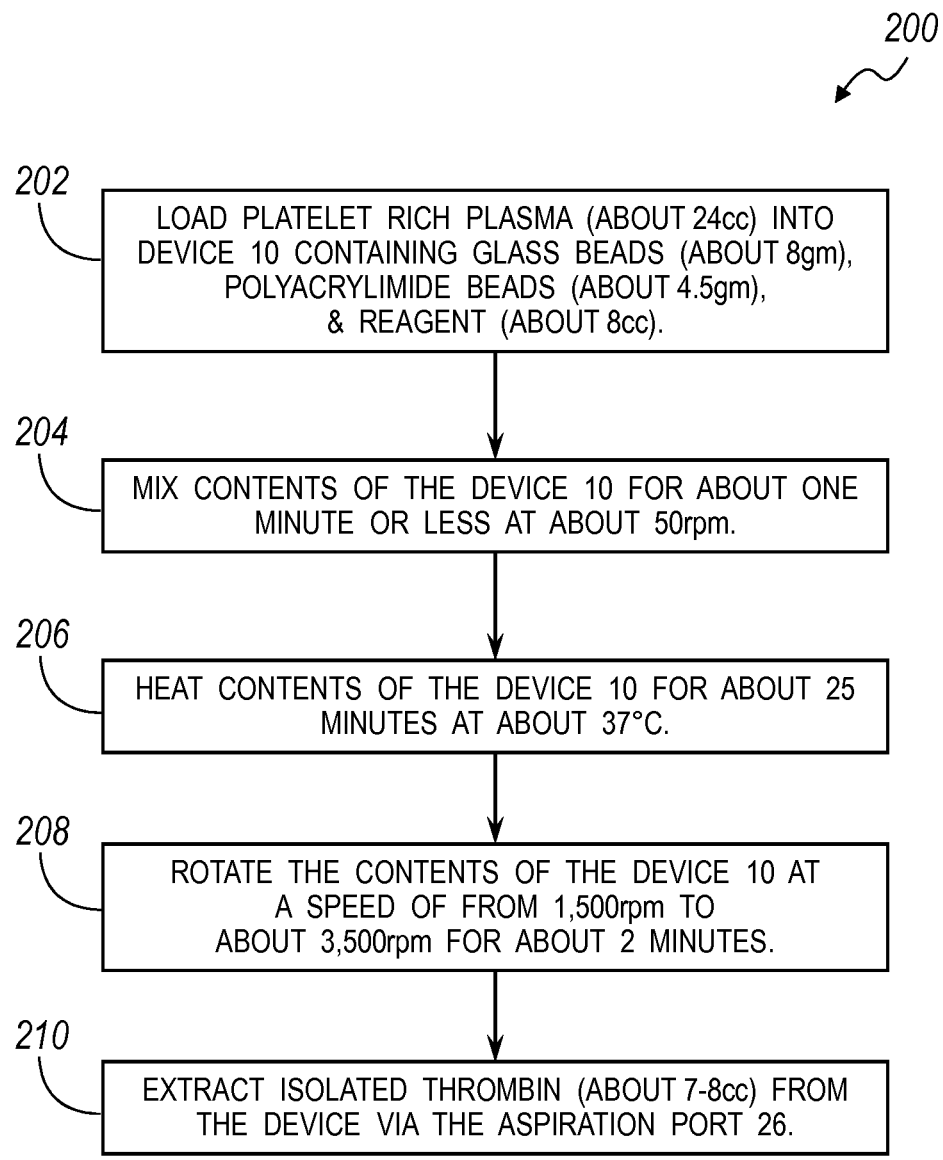
FIG. 7 illustrates a method according to the present teachings for isolating thrombin from platelet rich plasma.

With additional reference to FIG. 7, an additional method for isolating thrombin according to the present teachings will be described. With initial reference to block 202, a suitable amount of platelet rich plasma concentrate is loaded into the chamber 14 of the device 10. Any suitable amount of platelet rich plasma concentrate can be used, such as about 24 cc. The platelet rich plasma concentrate can be obtained using any suitable method or device, such as the device disclosed in United States Patent Publication No. 2006/0175244 (application Ser. No. 11/342,749) filed on Jan. 30, 2006, the Plasmax Plasma Concentrate Kit™ or the Vortech Concentration System™, all sold by Biomet Biologics, LLC of Warsaw, Ind. The platelet rich plasma concentrate can be isolated from autologous or non-autologous blood. The platelet rich plasma is loaded through the first inlet assembly 30. A suitable reagent, such as a calcium chloride and ethanol solution, is loaded into the chamber 14. The reagent is loaded through the second insert assembly 32.

Glass beads 58 and polyacrylimide beads 60 are included in the chamber 14. The beads 58 and 60 are typically loaded into the chamber 14 by the manufacturer. Any suitable amount of glass beads 58 and polyacrylimide beads 60 can be used, such as about 8 grams of glass beads and about 4.5 grams of polyacrylimide beads. The glass beads 58 facilitate activation of the blood platelets. After the whole blood and reagent are loaded into the chamber 14, the removable tubes 70 are removed from the first and the second inlet assemblies 30 and 32 to permit the chamber 14 to rotate freely in the housing 12.

At block 204, the platelet rich plasma, the glass beads 58, the polyacrylimide beads 60, and the reagent, which are all present in the chamber 14, are mixed. The contents of the chamber 14 are mixed by placing the device 10 on the annular support surface 88 of the torque generating device 16. Torque generated by the torque generating device 16 is transferred to the chamber 14 through the interaction between the motor connector 62 and the drive receptor 28 to rotate the chamber 14. The mixing paddle 46 facilitates mixing of the contents of the chamber 14. The presence of the glass beads 58 during rotation of the chamber 14 facilitates activation of the platelets.

At block 206, the contents of the chamber 14 are optionally heated or incubated by the heater 56 for about 25 minutes at about 37° C. The incubation process further activates the platelets to form a clot, thereby releasing thrombin. After the incubation process, the contents of the chamber 14 are rotated at a speed of from about 1,500 rpm to about 3,500 rpm for about 2 minutes at block 208. The polyacrylimide beads 60 remove excess water from the mixture to increase the concentration of thrombin provided. For example, use of about 4.5 grams of polyacrylimide beads 60 can result in thrombin that is about 6-7 times more concentrated than thrombin obtained without using such a quantity of polyacrylimide beads 60.

The rotation at an increased speed (block 208) causes thrombin to separate from the mixture and rise to the area of the filter 44. As set forth above, the filter 44 is sized to permit passage of the thrombin, but not other components of the mixture, such as the glass beads 58 and the polyacrylimide beads 60. The thrombin settles on the first portion 20a of the base portion 20 where it can be withdrawn from the device 10 through the aspiration port 26 using any suitable device, such as a syringe, at block 210. About 7-8 cc of thrombin can be obtained from about 24 cc of platelet rich plasma concentrate. Thus, the method 200 isolates thrombin that is of an increased concentration, such as about 6-7 times more concentrated, from platelet rich plasma derived from autologous or non-autologous blood. As set forth below, the isolated thrombin can be used in a variety of different ways to enhance the clotting and healing process.

The isolated thrombin can be used for a variety of different purposes. For example, the isolated thrombin can be loaded into a suitable sprayer device along with platelet poor plasma and introduced to a wound at a ratio of from about 5:1 to about 10:1 [thrombin to platelet poor plasma] to facilitate wound healing. The introduction of such a mixture to a wound facilitates clotting in as little as 15 seconds. The clotting process is expedited due to the presence of thrombin of increased concentration.

The isolated thrombin may also be used as a hemostatic agent and added directly to a wound or surgical site to enhance healing. Further, the isolated thrombin can be added to platelet gels, fibrin glues, plasma (platelet rich and platelet poor) to enhance their wound healing properties. For example, the isolated thrombin can be added to the plasma output of the Plasmax Plasma Concentrate Kit™ by Biomet Biologics, LLC of Warsaw, Ind.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A device for isolating a component of a multi-component composition comprising:
   a housing having a housing base;
   a chamber rotatably mounted within said housing such that the chamber is configured to be rotatable about its own axis, said chamber including:
      a chamber base; and
      a side wall extending from said chamber base, at least a portion of said sidewall is defined by a filter that permits passage of a first component of said multi-component composition out of said chamber through said filter and to said housing base, said filter is spaced apart from said chamber base, said filter restricts passage of a second component of said multi-component composition through said filter; and
   a withdrawal port that extends from a position proximate to said housing base to an exterior of said device, said withdrawal port permits the withdrawal of the first component from the housing base to an exterior of said device;
   wherein said chamber further comprises a fixed mixing paddle having a main portion that extends along an axis of rotation of said chamber and having two extending portions that extend from said main portion at about 180°, each of said extending portions include fins that protrude from said extending portions at right angles.

2. The device of claim 1, further comprising a torque generating device; and
   said chamber further comprising a drive receptor that cooperates with a motor connector of said torque generating device to transfer torque from said torque generating device to said chamber.

3. The device of claim 2, wherein said torque generating device includes a heater for heating contents of said chamber.

4. The device of claim 1, wherein said housing base includes a first sloped portion, a second sloped portion, and an apex portion between said first sloped portion and said second sloped portion;
   wherein said first sloped portion slopes toward a sidewall of said housing and said second sloped portion slopes away from said sidewall of said housing; and
   wherein said withdrawal port extends from a position proximate to said first sloped portion;
   wherein an annular rim extends from an undersurface of said chamber, said annular rim is proximate to said apex portion between said sidewall and said apex portion, said annular rim prevents said first component from passing over said apex portion.

5. The device of claim 1, further comprising glass beads and polyacrylimide beads within said chamber.

6. The device of claim 1, wherein said multi-component composition includes whole blood and said component isolated from said multi-component composition includes thrombin.

7. The device of claim 1, wherein said multi-component composition includes plasma and said component isolated from said multi-component composition includes thrombin.

8. The device of claim 1, wherein said multi-component composition includes platelet rich plasma concentrate and said component isolated from said multi-component composition includes thrombin.

9. The device of claim 1, wherein said filter includes openings sized to permit passage of the first component and restrict passage of the second component; and
   wherein said openings have a width of about 15 μm.

10. The device of claim 1, wherein said filter includes a polyester.

11. The device of claim 1, wherein said filter includes a polyethylene terephthalate monofilament.

12. The device of claim 1, wherein said filter includes a twill weave pattern.

13. The device of claim 1, wherein said filter includes a wire diameter of about 37 μm.

14. The device of claim 1, wherein said filter includes a thickness of about 55 μm.

15. A device for isolating a component of a multi-component composition comprising:

a housing having a housing base;
a chamber rotatably mounted within the housing such that the chamber is configured to be rotatable about its own axis, the chamber including:
  a chamber base;
  a chamber cover;
  a side wall extending from the chamber base to the chamber cover, at least a portion of the side wall is defined by a filter spaced apart from the chamber base and proximal to the chamber cover, the filter permits passage of a first component of the multi-component composition out of the chamber through the filter into the housing base, the filter restricts passage of a second component of the multi-component composition through the filter;
  glass beads and polyacrylimide beads within said chamber; and
  a withdrawal port that extends from a position proximate to the housing base to an exterior of the device, the withdrawal port permits withdrawal of the first component from the housing between an inner wall of the housing and the chamber to the exterior of the device.

16. A device for isolating a component of a multi-component composition comprising:
  a housing having a housing base, the housing base including a first sloped portion, a second sloped portion, and an apex portion between the first sloped portion and the second sloped portion, where the first sloped portion slopes toward a side wall of the housing and the second slope portion slopes away from the side wall of the housing;
  a chamber rotatably mounted within the housing such that the chamber is configured to be rotatable about its own axis, the chamber including:
    a chamber base;
    a side wall extending from the chamber base, at least a portion of the sidewall defining a plurality of passages to permit passage of a first component of the multi-component composition out of the chamber through the plurality of passages into the housing base, the plurality of passages spaced apart from the chamber base; and
    an annular rim that extends from an undersurface of the chamber, the annular rim proximate to the apex portion between the side wall and the apex portion; and
  a withdrawal port that extends from a position proximate to the housing base to an exterior of the device, the withdrawal port permits the withdrawal of the first component from the housing base to an exterior of the device.

17. A device for isolating a component of a multi-component composition comprising:
  a housing having a housing base;
  a chamber rotatably mounted within said housing, said chamber including:
    a chamber base; and
    a side wall extending from said chamber base, at least a portion of said sidewall is defined by a filter that permits passage of a first component of said multi-component composition out of said chamber through said filter and to said housing base, said filter restricts passage of a second component of said multi-component composition through said filter; and
  a withdrawal port that extends from a position proximate to said housing base to an exterior of said device, said withdrawal port permits the withdrawal of the first component from the housing base to an exterior of said device;
  wherein said housing base includes a first sloped portion, a second sloped portion, and an apex portion between said first sloped portion and said second sloped portion;
  wherein said first sloped portion slopes toward a sidewall of said housing and said second sloped portion slopes away from said sidewall of said housing; and
  wherein said withdrawal port extends from a position proximate to said first sloped portion.

18. A device for isolating a component of a multi-component composition comprising:
  a housing having a housing base and a housing cover;
  a first inlet assembly and a second inlet assembly;
  a chamber rotatably mounted within said housing, said chamber including:
    a chamber base;
    a side wall extending from said chamber base, at least a portion of said sidewall is defined by a filter that permits passage of a first component of said multi-component composition out of said chamber through said filter and to said housing base, said filter restricts passage of a second component of said multi-component composition through said filter; and
    a chamber cover; and
  a withdrawal port that extends from a position proximate to said housing base to an exterior of said device, said withdrawal port permits the withdrawal of the first component from the housing base to an exterior of said device;
  wherein said first inlet assembly and said second inlet assembly each extend through said housing cover and said chamber cover to provide a passageway from an exterior of said device to within said chamber, each of said first inlet assembly and said second inlet assembly include a removable inlet tube that prevent rotation of said chamber when inserted within said passageway.

19. A device for isolating a component of a multi-component composition comprising:
  a housing having a housing base;
  a chamber rotatably mounted within said housing such that the chamber is configured to be rotatable about its own axis, said chamber including:
    a chamber base; and
    a side wall extending from said chamber base, at least a portion of said sidewall is defined by a filter that permits passage of a first component of said multi-component composition out of said chamber through said filter and to said housing base, said filter is spaced apart from said chamber base, said filter restricts passage of a second component of said multi-component composition through said filter; and
  a withdrawal port that extends from a position proximate to said housing base to an exterior of said device, said withdrawal port permits the withdrawal of the first component from the housing base to an exterior of said device;
  a torque generating device, said chamber including a drive receptor that cooperates with a motor connector of said torque generating device to transfer torque from said torque generating device to said chamber; and
  a heater included with the torque generating device, the heater configured to heat contents of the chamber.

* * * * *